(12) United States Patent
Moloney

(10) Patent No.: US 10,604,710 B2
(45) Date of Patent: Mar. 31, 2020

(54) CORROSION INHIBITING COMPOSITIONS TO MITIGATE CORROSION IN ENVIRONMENTS CONTAINING ELEMENTAL SULFUR AND/OR POLYSULFIDES

(71) Applicant: Ecolab USA Inc., St. Paul, MN (US)

(72) Inventor: Jeremy Moloney, Katy, TX (US)

(73) Assignee: Ecolab USA Inc., St. Paul, MN (US)

( * ) Notice: Subject to any disclaimer, the term of this patent is extended or adjusted under 35 U.S.C. 154(b) by 214 days.

(21) Appl. No.: 15/442,198

(22) Filed: Feb. 24, 2017

(65) Prior Publication Data

US 2017/0247798 A1  Aug. 31, 2017

Related U.S. Application Data

(60) Provisional application No. 62/300,457, filed on Feb. 26, 2016.

(51) Int. Cl.

| *C10G 75/02* | (2006.01) |
| *C07C 211/01* | (2006.01) |
| *C23F 11/14* | (2006.01) |
| *C09K 8/54* | (2006.01) |
| *C23F 11/10* | (2006.01) |
| *C23F 11/16* | (2006.01) |
| *C10G 75/00* | (2006.01) |
| *C23F 11/04* | (2006.01) |
| *F16L 58/04* | (2006.01) |

(52) U.S. Cl.
CPC ............ *C10G 75/02* (2013.01); *C07C 211/01* (2013.01); *C09K 8/54* (2013.01); *C10G 75/00* (2013.01); *C23F 11/04* (2013.01); *C23F 11/10* (2013.01); *C23F 11/143* (2013.01); *C23F 11/145* (2013.01); *C23F 11/16* (2013.01); *C23F 11/164* (2013.01); *F16L 58/04* (2013.01)

(58) Field of Classification Search
CPC ..................... C07C 211/01; C10G 75/00–04
See application file for complete search history.

(56) References Cited

U.S. PATENT DOCUMENTS

| 3,412,024 | A | | 11/1968 | Stanford | |
| 3,703,477 | A | | 11/1972 | Jones | |
| 4,614,600 | A | * | 9/1986 | Schilling | C09K 8/54 |
| | | | | | 252/391 |
| 5,062,992 | A | | 11/1991 | McCullough | |
| 7,951,754 | B2 | | 5/2011 | Tiwari et al. | |
| 2009/0181867 | A1 | | 7/2009 | Yang et al. | |
| 2014/0076567 | A1 | * | 3/2014 | Meyer | C09K 8/54 |
| | | | | | 166/304 |
| 2015/0011453 | A1 | * | 1/2015 | Bennett | C11D 3/2006 |
| | | | | | 510/402 |
| 2015/0107832 | A1 | * | 4/2015 | DeWolf | C09K 8/52 |
| | | | | | 166/266 |

FOREIGN PATENT DOCUMENTS

GB        809 001 A      2/1959

OTHER PUBLICATIONS

International Search Report and Written Opinion issued for PCT/US2017/019447, dated May 23, 2017, 10 pages.
Extended European Search Report issued for EP 17757347.4 dated Sep. 9, 2019, 9 pages.

\* cited by examiner

*Primary Examiner* — Renee Robinson
(74) *Attorney, Agent, or Firm* — Stinson LLP

(57) ABSTRACT

A corrosion inhibiting composition is provided which comprises a salt of a fatty acid-amine condensate and an aromatic solvent. The composition can be used in reducing, inhibiting or preventing corrosion of a metal surface used in recovery, transportation, refining or storage of a hydrocarbon fluid containing elemental sulfur or polysulfide.

20 Claims, 3 Drawing Sheets

CORROSION INHIBITING COMPOSITIONS TO MITIGATE CORROSION IN ENVIRONMENTS CONTAINING ELEMENTAL SULFUR AND/OR POLYSULFIDES

CROSS REFERENCE TO RELATED APPLICATIONS

This application claims the benefit of U.S. Provisional Patent Application Ser. No. 62/300,457 filed on Feb. 26, 2016, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

The present invention generally relates to corrosion inhibitor compositions, and more particularly to compositions for reducing, inhibiting or preventing corrosion of a metal surface used in recovery, transportation, refining or storage of a hydrocarbon fluid containing elemental sulfur or polysulfide.

BACKGROUND OF THE INVENTION

Carbon steel pipelines transporting fluids containing elemental sulfur and/or polysulfides are known to be highly corrosive and extremely difficult to protect against corrosion. Typically, these highly sour systems are protected from pitting and general corrosion by adding large quantities of solvents which dissolve sulfur, or by adding corrosion inhibitor compositions. The corrosion inhibitor compositions and solvents can be expensive and if used in large quantities can give rise to various issues in the production system such as emulsification and foaming problems.

There is a continuing need for compositions effective in inhibiting corrosion in such highly corrosive environments.

BRIEF SUMMARY OF THE INVENTION

A corrosion inhibiting composition is provided which comprises a salt of a fatty acid-amine condensate and an aromatic solvent.

A corrosion-inhibiting composition is provided which comprises from about 2 to about 30 wt. % of a salt of a fatty acid-amine condensate; from about 1 to about 40 wt. % cationic surfactant; from about 1 to about 40 wt. % substituted aromatic amine; from about 1 to about 30 wt. % phosphoric acid ester; from 0 to about 20 wt. % solvent stabilizer compound; from 0 to about 5 wt. % demulsifier; from 0 to about 15 wt. % organic sulfur compound; and from about 40 to about 80 wt. % aromatic solvent.

A method is provided for reducing, inhibiting or preventing corrosion of a metal surface used in recovery, transportation, refining or storage of a hydrocarbon fluid containing elemental sulfur or polysulfide. The method comprises contacting the corrosion-inhibiting composition with the metal surface to reduce, inhibit or prevent corrosion of the metal surface.

Other objects and features will be in part apparent and in part pointed out hereinafter.

BRIEF DESCRIPTION OF THE SEVERAL VIEWS OF THE DRAWING

Corresponding reference characters indicate corresponding parts throughout the drawings.

DETAILED DESCRIPTION OF THE INVENTION

Figure 1:
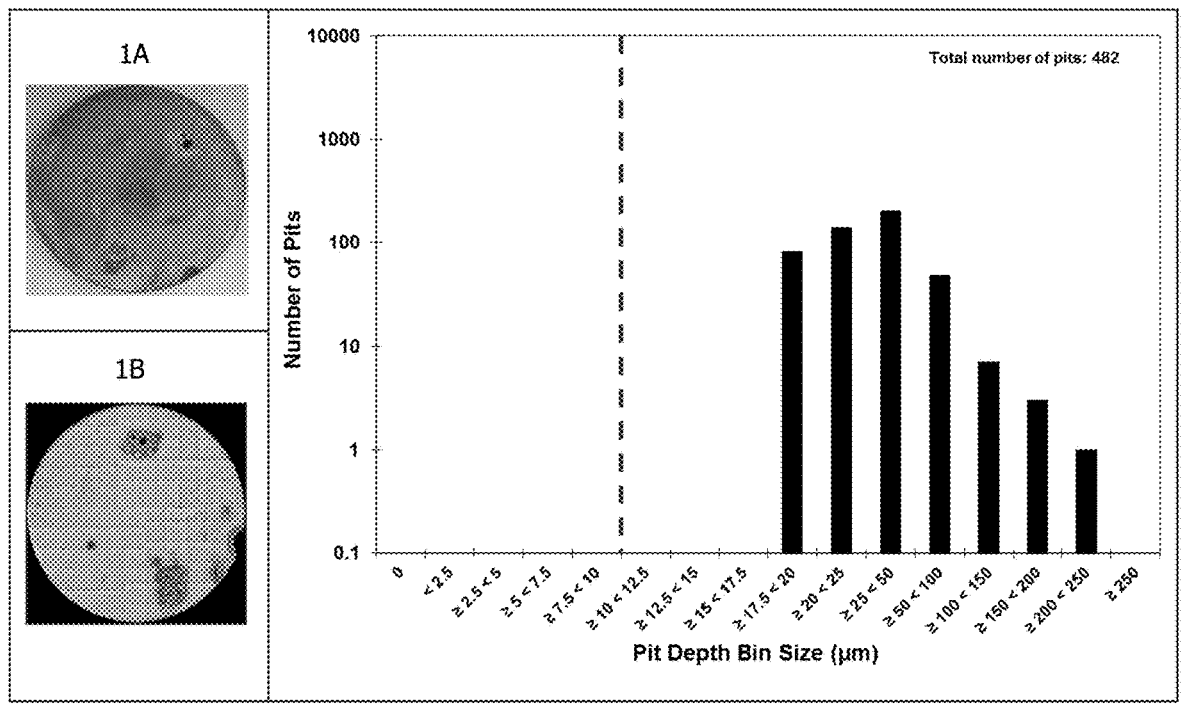
FIG. 1 depicts a photograph of a coupon surface after corrosion testing (panel 1A), a WLI microscopic image of the coupon surface after corrosion testing (panel 1B), and a pit histogram indicating the total number of pits in a particular depth range for the coupon for Comparative Composition D under the first set of test conditions at 5,000 ppm concentration.
Figure 2:
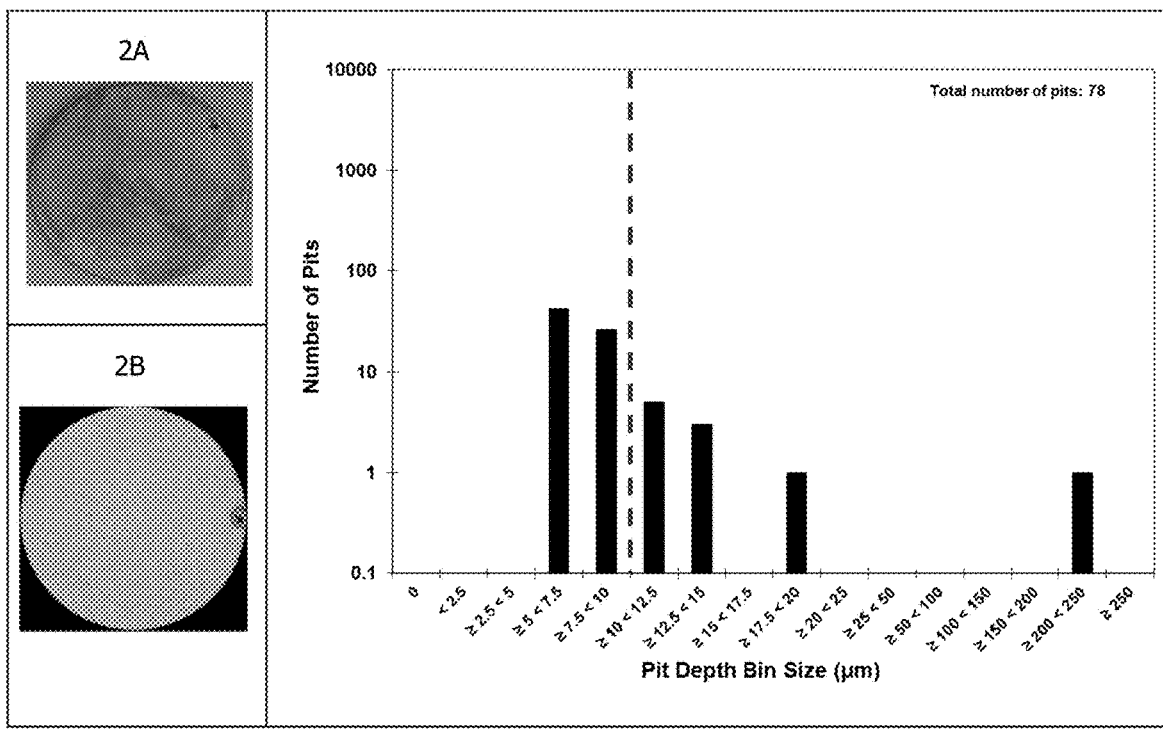
FIG. 2 shows a photograph of a coupon surface after corrosion testing (panel 2A), a WLI microscopic image of the coupon surface after corrosion testing (panel 2B), and a pit histogram indicating the total number of pits in a particular depth range for the coupon for Comparative Composition D under the first set of test conditions at 10,000 ppm concentration.
Figure 3:
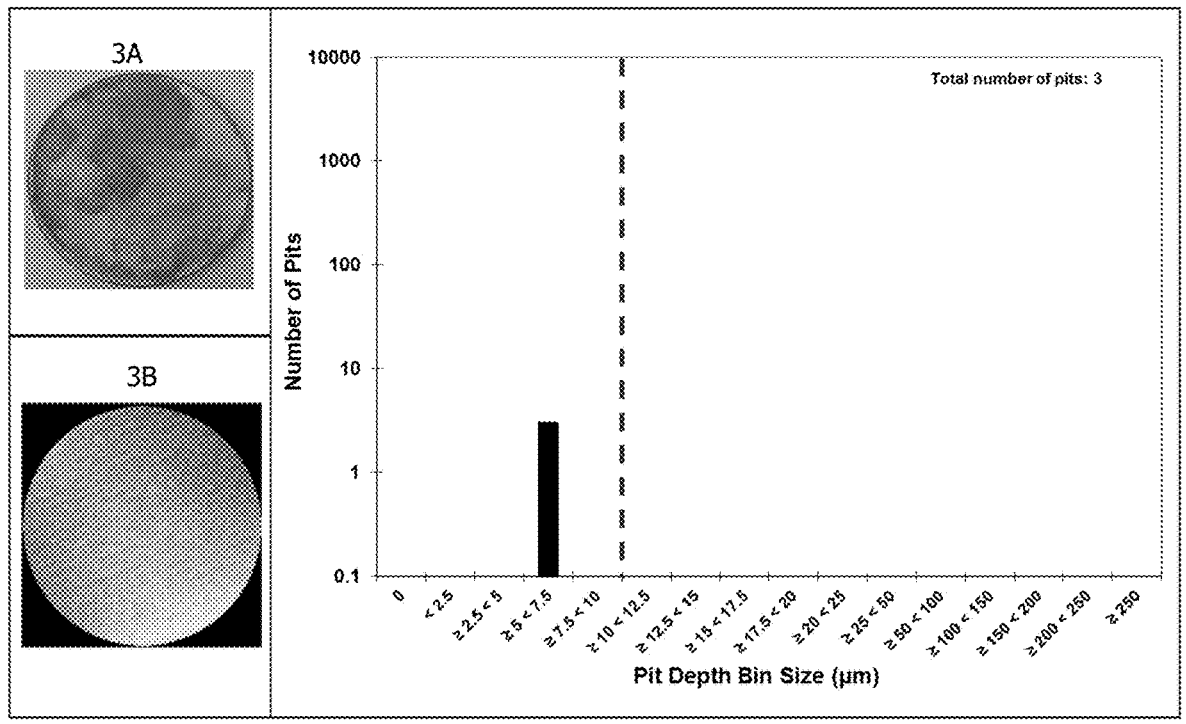
FIG. 3 depicts a photograph of a coupon surface after corrosion testing (panel 3A), a WLI microscopic image of the coupon surface after corrosion testing (panel 3B), and a pit histogram indicating the total number of pits in a particular depth range for the coupon for Composition A under the first set of test conditions at 5,000 ppm concentration.
Figure 4:
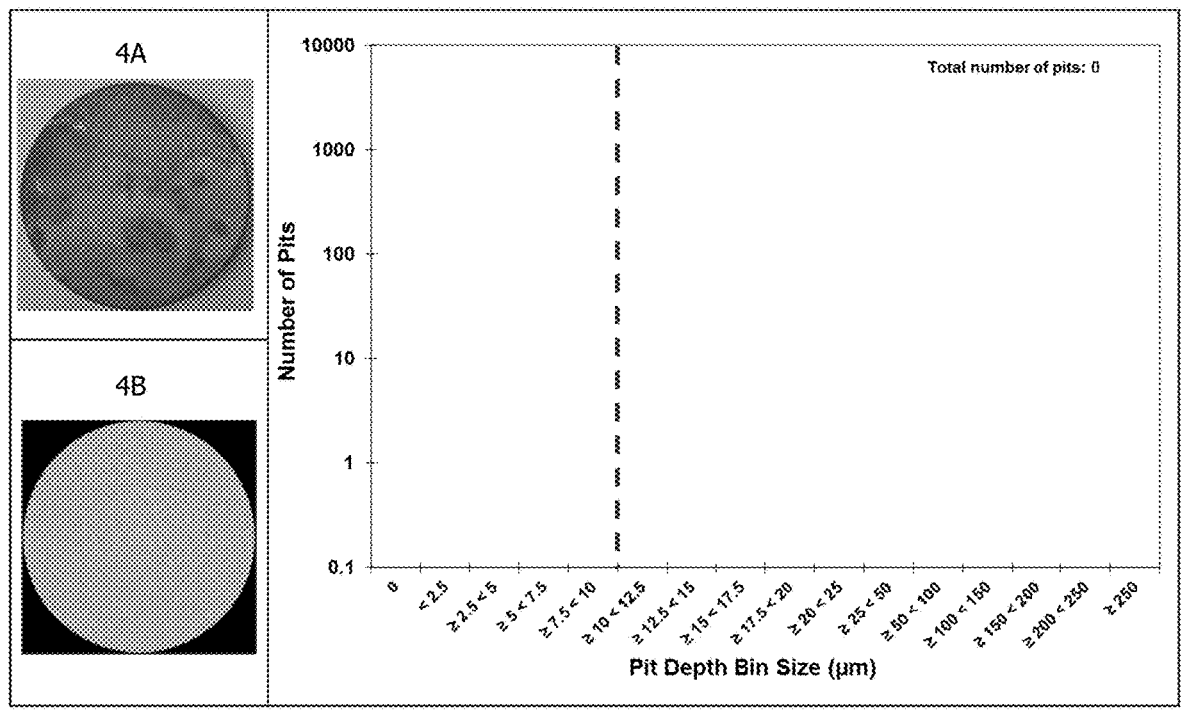
FIG. 4 depicts a photograph of a coupon surface after corrosion testing (panel 4A), a WLI microscopic image of the coupon surface after corrosion testing (panel 4B), and a pit histogram indicating the total number of pits in a particular depth range for the coupon for Composition B under the first set of test conditions at 5,000 ppm concentration.

Corrosion inhibitor compositions have been discovered which are particularly effective for reducing, inhibiting or preventing corrosion of a metal surface used in recovery, transportation, refining or storage of a hydrocarbon fluid containing elemental sulfur or polysulfide. The compositions can be used in systems having sour conditions (i.e., relatively high hydrogen sulfide concentration) but can also be used in sweet systems (i.e., systems having a relatively high carbon dioxide concentration). The compositions are useful in treating sour systems in a wide range of climates and under a wide range of process conditions, (e.g., 0° C. to 200° C.), where conventional corrosion inhibitor compositions fail, particularly with respect to pitting corrosion.

The compositions can provide greater than or equal to 90 or 95% corrosion protection. The compositions can provide at least 95% corrosion protection after 137 hours for a carbon steel working electrode (e.g., a 1018 carbon steel working electrode) in a high pressure sour corrosion test, wherein the high pressure sour corrosion test is characterized by a testing temperature of about 50° C.; a carbon dioxide saturated liquid medium of synthetic brine containing 770 ppm elemental sulfur and 1,000 ppm sodium tetrasulfide; and an inhibitor dosage of 3,000 ppm based on total fluids.

The compositions comprise a salt of a fatty acid-amine condensate and an aromatic solvent.

The salt of a fatty acid-amine condensate can comprise a reaction product of (1) a polyunsaturated fatty acid dimer, (2) a sulfonic acid compound, and (3) a reaction product of a polyalkylene polyamine, a tall oil fatty acid, and a polyunsaturated fatty acid dimer. A preferred salt of a fatty acid-amine condensate is commercially available as tall oil acid, dimeric linoleic acid, poly C2-C4 alkylene polyamine condensate, dodecylbenzene sulfonic acid, dimeric linoleic acid salts (CAS 68910-85-0).

The polyunsaturated fatty acid dimer (or the polyunsaturated fatty acid dimer of the reaction product (3) above) can independently comprise a dimer of linoleic acid, gamma-linolenic acid (GLA), eicosadienoic acid, dihomo-gamma-linolenic acid (DLGA), arachidonic acid (AA), docosadienoic acid, adrenic acid, docosapentaenoic acid, tetracosatetraenoic acid, tetracosapentaenoic acid, hexadecatrienoic acid (HTA), alpha-linolenic acid (ALA), stearidonic acid (SDA), eicosatrienoic acid (ETE), eicosatetraenoic acid (ETA), eicosapentaenoic acid (EPA), heneicosapentaenoic acid (HPA), docosapentaenoic acid (DPA), docosahexaenoic acid (DHA), tetracosapentaenoic acid, tetracosahexaenoic acid, mead acid, or a combination thereof. Preferably, the polyunsaturated fatty acid dimer comprises linoleic acid dimer.

The sulfonic acid compound can comprise an organic sulfonic acid. The organic sulfonic acid can be an aryl sulfonic acid including, but not limited to, a linear alkylbenzenesulfonic acid, a branched alkylbenzenesulfonic acid, or other substituted or unsubstituted aromatic sulfonic acid. Suitable aryl sulfonic acids include, but are not limited to, methylbenzene sulfonic acid (e.g., p-toluenesulfonic acid), ethylbenzene sulfonic acid, butylbenzene sulfonic acid, octylbenzene sulfonic acid, dodecylbenzene sulfonic acid, and 2-naphthalene sulfonic acid. Preferably, the sulfonic acid compound comprises a linear alkyl benzene sulfonic acid such as dodecylbenzene sulfonic acid.

The organic sulfonic acid can also comprise an alkyl sulfonic acid or an arylalkyl sulfonic acid including, but not limited to methanesulfonic acid, trifluoromethanesulfonic acid, DL-camphorsulfonic acid, and phenylmethanesulfonic acid.

The organic sulfonic acid can include a monosulfonic acid, a disulfonic acid, or a polysulfonic acid. Suitable disulfonic acids include, but are not limited to, benzenedisulfonic acid, napthalenedisulfonic acid, 2,3-dimethyl-1,4-benzenedisulfonic acid, 2,4-dimethyl-1,3-benzenedisulfonic acid, 2,5-dimethyl-1,3-benzenedisulfonic acid, 2,5-dimethyl-1,4-benzenedisulfonic acid, 3,6-dimethyl-1,2-benzenedisulfonic acid, or a combination thereof. Suitable polysulfonic acids include, but are not limited to, benzene trisulfonic acid, naphthalene trisulfonic acid, 1,3,6-napthalenetrisulfonic acid, 1-nitronaphthalene-3,6,8-trisulfonic acid, or a combination thereof.

The polyalkylene polyamine of the reaction product (3) above can include, but is not limited to, a polyethylene polyamine, a polypropylene polyamine, a polybutylene polyamine, and a combination thereof. Preferably, the polyalkylene polyamine comprises a combination of polyethylene polyamine, polypropylene polyamines, and polybutylene polyamines.

Suitable polyethylene polyamines include, but are not limited to, diethylene triamine (DETA), triethylene tetramine (TETA), tetraethylene pentamine (TEPA), pentaethylene hexamine (PEHA), hexaethylene heptamine (HEHA), and higher homologues.

Suitable polypropylene polyamines include, but are not limited to, dipropylene triamine, tripropylene tetramine, tetrapropylene pentamine, pentapropylene hexamine, hexapropylene heptamine, and higher homologues.

Suitable polybutylene polyamines include, but are not limited to, dibutylene triamine, tributylene tetramine, tetrabutylene pentamine, pentabutylene hexamine, hexabutylene heptamine, and higher homologues.

Other suitable polyalkylene polyamines include bis(hexamethylene)triamine, N,N'-bis(3-aminopropyl)ethylenediamine, spermidine, and spermine.

It will be recognized by those skilled in the art that polyalkylene polyamines containing four or more nitrogen atoms are generally available as mixtures of linear, branched, and cyclic compounds, most of which contain the same number of nitrogen atoms. For example, triethylene tetramine (TETA) contains not only linear TETA, but also tris(aminoethyl)amine, N,N'-bis(2-aminoethyl)piperazine, and N-[(2-aminoethyl)-2-aminoethyl]piperazine. Similarly, tetraethylene pentamine is principally a mixture of four TEPA ethyleneamines, including linear, branched, and two cyclic TEPA products.

A suitable polyalkylene polyamine is Ethyleneamine E-100, a commercially available mixture of polyethylene polyamines comprising TEPA, PEHA, and HEHA (Huntsman Corporation). Ethyleneamine E-100 typically consists of less than 1.0 wt. % of low molecular weight amine, 10-15 wt. % TEPA, 40-50 wt. % PEHA, and the balance HEHA and higher oligomers. Typically, Ethyleneamine E-100 has total nitrogen content of about 33-34 wt. % and a number average molecular weight of 250-300 g/mole.

A suitable polyamine mixture is Heavy Polyamine X (HPA-X), commercially available from Dow Chemical Company. Heavy Polyamine X is a complex mixture of linear, branched, and cyclic polyethylene polyamines, comprising TETA, TEPA, PEHA, and polyethylene polyamines (CAS No. 68131-73-7 or CAS No. 29320-38-5).

Another suitable polyamine mixture is Amix 1000 (CAS #68910-05-4), commercially available from BASF Corporation. Amix 1000 is a mixture of roughly equivalent amounts of aminoethylethanolamine, triethylene tetramine (TETA), aminoethylpiperazine, and high boiling polyamines.

The tall oil fatty acid of the reaction product (3) above can comprise any tall oil fatty acid including, but not limited to, oleic acid, linoleic acid, abietic acid, neoabietic acid, palustric acid, pimaric acid, dehydroabietic acid, palmitic acid, stearic acid, palm itoleic acid, 5,9,12-octadecatrienoic acid, linolenic acid, 5,11,14-eicosatrenoic acid, cis,cis-5,9-octadecadienoic acid, eicosadienoic acid, elaidic acid, cis-11-octadecanoic acid, or a combination thereof, as well as other $C_{20}$, $C_{22}$, $C_{24}$ saturated acids.

The salt of the fatty acid-amine condensate can be present in an amount of about 2 to about 30 wt. % based on total weight of the composition, preferably about 3 to about 20 wt. %, and more preferably about 4 to about 10 wt. %. The salt of the fatty acid-amine condensate can constitute about 2, 5, 10, 15, 20, 25 or 30 wt. % of the composition.

The aromatic solvent can comprise aromatic hydrocarbons such as toluene, xylene, heavy aromatic naphtha, or a combination thereof. Preferably, the aromatic solvent comprises heavy aromatic naphtha or xylene. The solvent can be present in an amount of about 40 to about 80 wt. %, based on total weight of the composition, preferably about 50 to about 80 wt. % and more preferably about 65 to about 80 wt. %. The solvent can constitute about 40, 45, 50, 55, 60, 65, 70, 75, or 80 wt. % of the composition.

The substituted aromatic amine can comprise an alkyl pyridine such as 3,5-diethyl-2-methylpyridine or 3-ethyl-4-methylpyridine, or other substituted pyridines such as (E)-5-ethyl-2-(prop-1-en-1-yl)pyridine, (E)-5-(but-2-en-1-yl)-2-methylpyridine, or N-ethyl-2-(6-methylpyridin-3-yl)ethanamine. A combination of such alkyl pyridines and substituted pyridines is commercially available as Akolidine™ 11 from Lonza. The substituted aromatic amine can be present in an amount of about 1 to about 40 wt. %, based on total weight of the composition, preferably about 1 to about 20 wt. % and more preferably about 1 to about 10 wt. %. The substituted aromatic amine can constitute about 1, 5, 10, 15, 20, 25, 30, 35 or 40 wt. % of the composition.

The composition can further comprise a cationic surfactant. The cationic surfactant can include, but is not limited to, alkoxylated alkyl amine, a quaternary ammonium compound, or a combination thereof. The cationic surfactant can constitute about 1 to about 40 wt. % of the composition, based on the total weight of the composition, preferably about 1 to about 20 wt. %, and more preferably about 1 to about 10 wt. %. The cationic surfactant can constitute 1, 2, 3, 4, 5, 6, 7, 8, 9, 10, 15, 20, 25, 30, 35 or 40 wt. % of the composition.

The alkoxylated alkyl amine can comprise an ethoxylated alkyl amine such as ethoxylated tallow amine. The alkoxylated alkyl amine can constitute about 1 to about 20 wt. % of the composition, based on the total weight of the composition, preferably about 1 to about 10 wt. %, and more preferably about 1 to about 5 wt. %. The alkoxylated alkyl amine can constitute 1, 2, 3, 4, 5, 6, 7, 8, 9, 10, 15 or 20 wt. % of the composition.

The quaternary ammonium compound can be a pyridinium salt such as those represented by Formula (I):

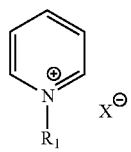

(I)

wherein $R_1$ is a $C_1$-$C_{18}$ alkyl group, an aryl group, or an arylalkyl group, and $X^-$ is chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium and a $C_1$-$C_6$ alkyl benzyl pyridinium chloride. Preferably, the pyridinium salt includes $C_1$-$C_6$ alkyl benzyl pyridinium chloride. The pyridinium salt can constitute about 1 to about 40 wt. % of the composition, based on total weight of the composition, preferably about 1 to about 20 wt. % and more preferably about 1 to about 10 wt. %. The pyridinium salt can constitute 1, 2, 3, 4, 5, 6, 7, 8, 9, 10, 15, 20, 25, 30, 35 or 40 wt. % of the composition.

The quaternary ammonium compound can comprise an imidazolinium compound of Formula (II):

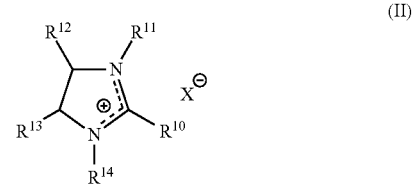

(II)

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently a $C_1$-$C_6$ alkyl group or hydrogen; and $X^-$ is chloride, bromide, iodide, carbonate, sulfonate, phosphate, or the anion of an organic acid such as acetate. Preferably, the imidazolinium salt includes 1-benzyl-1-(2-hydroxyethyl)-2-tall-oil-2-imidazolinium chloride. The imidazolinium salt can constitute 1 to 30 wt. % of the composition, based on total weight of the composition, preferably about 1 to about 20 wt. % and more preferably about 1 to about 10 wt. %. The imidazolinium salt can constitute 1, 2, 3, 4, 5, 6, 7, 8, 9, 10, 15, 20, 25, or 30 wt. % of the composition.

The cationic surfactant can comprise 2-alkyl-1-benzyl-1-(2-hydroxyethyl)-2-imidazolium chloride (e.g., $C_{12}$-, $C_{14}$-, $C_{16}$-, and/or $C_{18}$-alkyl-1-benzyl-1-(2-hydroxyethyl)-2-imidazolium chloride), N-benzylpyridinium chloride (e.g., N-benzyl-pyridinium chloride, N-benzyl $C_1$-$C_6$ alkyl pyridinium chloride, N-benzyl-picolinium chloride), ethoxylated tallow amine, or a combination thereof.

Preferably, the cationic surfactant comprises a mixture of 1-benzyl-1-(2-hydroxyethyl)-2-tall oil-2-imidazolinium chloride, N-benzyl-pyridinium chloride or N-benzyl $C_1$-$C_6$ alkyl pyridinium chloride, and ethoxylated tallow amine in about equal relative proportions, based on the total weight of the cationic surfactant.

The composition can further comprise a solvent stabilizer. Preferably, the solvent stabilizer includes a glycol ether including, but not limited to, 2-butoxyethanol, diethyleneglycol monomethyl ether, ethylene glycol monobutyl ether, ethylene glycol dibutyl ether, or a combination thereof. Preferably, the solvent stabilizer comprises 2-butoxyethanol. The solvent stabilizer can constitute about 1 to 20 wt. % of the composition, based on total weight of the composition, preferably about 1 to about 15 wt. % and more preferably about 1 to about 10 wt. %. The solvent stabilizer can constitute 1, 2, 3, 4, 5, 6, 7, 8, 9, 10, 15, or 20 wt. % of the composition.

The composition can further comprise a phosphoric acid ester. Preferably, the phosphoric acid ester comprises an alkoxylated alkylphenol phosphate ester. Preferably, the alkoxylated alkylphenol phosphate ester comprises an ethoxylated nonylphenol phosphate ester. The phosphoric acid ester can constitute about 1 to 30 wt. % of the composition, based on total weight of the composition, preferably about 1 to about 20 wt. % and more preferably about 1 to about 10 wt. %. The phosphoric acid ester can constitute 1, 2, 3, 4, 5, 6, 7, 8, 9, 10, 15, 20, 25, or 30 wt. % of the composition.

The composition can further comprise an organic sulfur compound, such as a mercaptoalkyl alcohol, mercaptoacetic acid, thioglycolic acid, 3,3'-dithiodipropionic acid, thiosulfate, thiourea, L-cysteine, or tert-butyl mercaptan. Preferably, the mercaptoalkyl alcohol comprises 2-mercaptoethanol. The organic sulfur compound can constitute 0 to 15 wt. % of the composition, based on total weight of the composition, preferably about 1 to about 10 wt. % and more preferably about 1 to about 5 wt. %. The solvent stabilizer can constitute 1, 2, 3, 4, 5, 6, 7, 8, 9, 10, 11, 12, 13, 14 or 15 wt. % of the composition.

The composition can further include a demulsifier, such as an oxyalkylate polymer, dodecylbenzylsulfonic acid (DDBSA), the sodium salt of xylenesulfonic acid, epoxylated and propoxylated compounds, phenolic and epoxide resins, and combinations thereof. Preferably, the demulsifier comprises an oxyalkylate polymer, such as a polyalkylene glycol. The demulsifier can constitute 0.5 to 5 wt. % of the composition, based on total weight of the composition. The demulsifier can constitute 0.5, 1, 1.5, 2, 2.5, 3, 3.5, 4, 4.5 or 5 wt. % of the composition.

Thus, a corrosion-inhibiting composition is provided comprising from about 2 to about 30 wt. % of a salt of a fatty acid-amine condensate; from about 1 to about 40 wt. % cationic surfactant; from about 1 to about 40 wt. % substituted aromatic amine; from about 1 to about 30 wt. % phosphoric acid ester; from about 1 to about 20 wt. % solvent stabilizer compound; from about 0.5 to about 5 wt. % demulsifier; from 0 to about 15 wt. % organic sulfur compound; and from about 40 to about 80 wt. % aromatic solvent. Preferably, the composition comprises from about 3 to about 20 wt. % of the salt of a fatty acid-amine condensate; from about 1 to about 20 wt. % of the cationic surfactant; from about 1 to about 20 wt. % of the substituted aromatic amine; from about 1 to about 20 wt. % of the phosphoric acid ester; from about 1 to about 15 wt. % of the solvent stabilizer compound; from about 0.5 to about 5 wt. % of the demulsifier; from 1 to about 10 wt. % of the organic sulfur compound; and from about 50 to about 80 wt. % of the aromatic solvent. More preferably, the composition comprises from about 4 to about 10 wt. % of the salt of a fatty acid-amine condensate; from about 1 to about 10 wt. % of the cationic surfactant; from about 1 to about 10 wt. % of the substituted aromatic amine; from about 1 to about 10 wt. % of the phosphoric acid ester; from about 1 to about 10 wt. % of the solvent stabilizer compound; from about 0.5 to about 5 wt. % of the demulsifier; from 1 to about 5 wt. % of the organic sulfur compound; and from about 65 to about 80 wt. % of the aromatic solvent.

The compositions can optionally include one or more additives. Suitable additives include, but are not limited to, asphaltene inhibitors, paraffin inhibitors, scale inhibitors, emulsifiers, water clarifiers, dispersants, emulsion breakers, hydrogen sulfide scavengers, gas hydrate inhibitors, biocides, pH modifiers, and surfactants.

Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable dispersants include, but are not limited to, dodecyl benzene sulfonate, oxyalkylated alkylphenols, and oxyalkylated alkylphenolic resins.

Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetraminepolymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; and triazines (e.g., monoethanolamine triazine, monomethylamine triazine, and triazines from multiple amines or mixtures thereof).

Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Compositions made according to the invention can further include additional functional agents or additives that provide a beneficial property. The amount of an additional agent or additive, when present, will vary according to the particular composition being manufactured and its intended use as one skilled in the art will appreciate.

The compositions can be prepared by combining the components as described above.

The compositions can be used for reducing, inhibiting or preventing corrosion of a metal surface used in recovery, transportation, refining or storage of a hydrocarbon fluid containing elemental sulfur or polysulfide. The method comprises contacting any of the compositions described herein with the metal surface to reduce, inhibit or prevent corrosion of the metal surface.

The compositions can be used for inhibiting corrosion by treating the hydrocarbon fluid containing elemental sulfur or polysulfide with an effective amount of the composition, such as, for example, a concentration of about 100 to about 10,000 ppm of the composition in the hydrocarbon fluid.

The compositions can be used in any industry where it is desirable to inhibit corrosion from a metal surface which comes in contact with the hydrocarbon fluid.

The hydrocarbon fluid can be any type of liquid hydrocarbon including, but are not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The fluid can be a refined hydrocarbon product.

The composition can be added to the hydrocarbon fluid before the hydrocarbon fluid contacts the metal surface.

The metal surface can comprise a carbon steel conduit or pipeline.

The hydrocarbon fluid can contain elemental sulfur, a polysulfide, or a combination thereof. The hydrocarbon fluid can contain 10, 20, 30, 40, 50, 60, 70, 80, 90, 100, 200, 300, 400, 500, 600, 700, 800, 900 1,000 or more ppm of elemental sulfur and/or 10, 20, 30, 40, 50, 60, 70, 80, 90, 100, 200, 300, 400, 500, 600, 700, 800, 900 1,000 or more ppm of a polysulfide, such as sodium tetrasulfide.

The compositions can be used in water systems, condensate/oil systems/gas systems, or any combination thereof. The compositions can be applied to a gas or liquid produced, or used in the production, transportation, storage, refining and/or separation of crude oil or natural gas. The compositions can be applied to a gas stream used or produced in a coal-fired process, such as a coal-fired power plant. The compositions can be applied to a gas or liquid produced or used in a waste-water process, a farm, a slaughter house, a land-fill, a municipality waste-water plant, a coking coal process, or a biofuel process.

A fluid to which the compositions can be introduced can be an aqueous medium. The aqueous medium can comprise water, gas, and optionally liquid hydrocarbon. A fluid to which the compositions can be introduced can be a liquid hydrocarbon.

A fluid or gas treated with the composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C.

to 90° C. The fluid or gas can be at a temperature of −50° C., −45° C., −40° C., −35° C., −30° C., −25° C., −20° C., −15° C., −10° C., −5° C., or 0° C. The fluid or gas can be found in an arctic environment, and can have a temperature and salinity typical of such environment.

The compositions of the invention can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1 to 24%, or about 10% to 25% weight/weight (w/w) total dissolved solids (TDS).

The fluid or gas in which the composition is introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The composition can be introduced to large diameter flow lines of from about 1 inch to about 4 feet in diameter, small gathering lines, small flow lines and headers. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units. The fluid or gas can be contained in water systems, condensate/oil systems/gas systems, or any combination thereof.

The composition can be introduced into a fluid or gas by any appropriate method for ensuring dispersal through the fluid or gas. The composition can be added at a point in a flow line upstream from the point at which corrosion prevention is desired. The compositions can be injected using mechanical equipment such as chemical injection pumps, piping tees, injection fittings, atomizers, quills, and the like.

The composition can be pumped into an oil and/or gas pipeline using an umbilical line. A capillary injection system can be used to deliver the composition to a selected fluid. The compositions can be introduced into a liquid and mixed. The composition can be injected into a gas stream as an aqueous or non-aqueous solution, mixture, or slurry. The fluid or gas can be passed through an absorption tower comprising the composition.

The composition can be applied to a hydrocarbon fluid to provide any selected concentration. In practice, the composition is typically added to a flow line to provide an effective treating dose of from about 100 to about 1,000,000 ppm preferably from about 500 to about 100,000 ppm, and more preferably from about 500 to about 10,000 ppm. Each system can have its own requirements, and the effective amount of a composition to sufficiently reduce the rate of corrosion can vary with the system in which it is used.

The compositions can be applied continuously, in batch, or a combination thereof. For example, the composition doses can be continuous to prevent corrosion or intermittent (i.e., batch treatment). The composition doses can be continuous/maintained and/or intermittent to inhibit corrosion. Dosage rates for continuous treatments typically range from about 10 to about 5,000 ppm. Dosage rates for batch treatments typically range from about 500 to about 10,000 ppm. The composition can also be applied as a pill to a pipeline, providing a high dose (e.g., up to 1,000,000 ppm) of the composition.

The flow rate of a flow line in which the composition is used can be between 0 and 100 feet per second, or between 0.1 and 50 feet per second. The compositions can be formulated with water in order to facilitate addition to the flow line.

Having described the invention in detail, it will be apparent that modifications and variations are possible without departing from the scope of the invention defined in the appended claims.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only, and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional steps or components. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups can be unsubstituted or substituted by one or more suitable substituents, as defined above.

EXAMPLES

The following non-limiting examples are provided to further illustrate the present invention.

Compositions A-I, which include a salt of a fatty acid-amine condensate, are prepared and tested as compared to a similar Comparative Composition J which does not include a salt of a fatty acid-amine condensate. Comparative Composition K also does not include a salt of a fatty acid-amine condensate and is the incumbent best corrosion inhibiting composition for highly sour carbon steel pipeline systems. The compositions A-K are shown in Table 1:

TABLE 1

| | | Composition (wt. %) | | | | | | | | | Comparative Composition |
|---|---|---|---|---|---|---|---|---|---|---|---|
| Component | | | | | | | | | | | |
| Genus | Species | A | B | C | D | E | F | G | H | I | J |
| Aromatic solvent | Heavy aromatic naphtha | | | 61 | | | 73 | | | 80 | |
| | Xylene | | 55 | | | 70 | | | 73 | | |
| | Toluene | 52 | | | 63 | | | 75 | | | |
| Solvent | Methanol | | | | | | | | | | 74.7 |
| Solvent stabilizer | diethyleneglycol monomethyl ether | | 8 | | 5 | | | 2 | | 1 | |
| | ethylene glycol monobutyl ether | 10 | | | | 4 | | | | | |
| | 2-butoxyethanol | | | 6 | | | 2.8 | | 2.8 | | 3.16 |
| Substituted aromatic amine | Alkylpyridine | 10 | 7.7 | 5 | 7 | 5 | 6 | 3 | 6 | 1.5 | 7.59 |
| Cationic surfactant | N-Benzyl alkylpyridinium chloride | | | | | 2.5 | | 2 | | 2 | |
| | 1-Benzyl-1-(2-hydroxyethyl)-2-tall oil-2-imidazolinium chloride | | | | | | | 2 | | 2 | |
| | N-benzyl pyridinium chloride | 1 | | | | 3 | | | | 2 | |
| | Octyl pyridinium chloride | | 7.3 | | 2.5 | | | | | | |
| | N-benzyl-picolinium chloride | | | | | | | | 10 | 3 | |
| | Naphthenic acid imidazoline acetate | | | 5 | | | | | | | 7.59 |
| | Ethoxylated tallow amine | | | | | 3 | 2 | | 2 | | |
| Phosphoric acid ester | Ethoxylated nonylphenol phosphate ester | 10 | 8 | | | 5 | | 2 | | 1 | |
| | Ethoxylated branched nonylphenol phosphate ester | | | 7 | 6 | | 3 | | 3 | | 3.8 |
| Salt of a fatty acid-amine condensate | Reaction product of (1) a linoleic acid dimer, (2) dodecyl benzyl sulfonic acid, and (3) a reaction product of a polyalkylene polyamine, a tall oil fatty acid, and a linoleic acid dimer | | | | 8 | | 5 | | 5 | | |
| Salt of a fatty acid-amine condensate | Reaction product of (1) a gamma-linoleic acid dimer, (2) octylbenzene benzyl sulfonic acid, and (3) a reaction product of a polyalkylene polyamine, a tall oil fatty acid, and a gamma-linoleic acid dimer | | | | | | 3 | | | | |
| | Reaction product of (1) an eicosadienoic dimer, (2) butylbenzene sulfonic acid, and (3) a reaction product of a polyalkylene polyamine, a tall oil fatty acid, and an eicosadienoic dimer | | | | 7 | | | | | | |
| | Reaction product of (1) a DLGA dimer, (2) 2-naphthalene sulfonic acid, and (3) a reaction product of a polyalkylene polyamine, a tall oil fatty acid, and a gamma-linoleic acid dimer | | | | | | | | | 10 | |
| | Reaction product of (1) an alpha-linolenic acid dimer, (2) methylbenzene sulfonic acid, and (3) a reaction product of a polyalkylene polyamine, a tall oil fatty acid, and an alpha-linolenic acid dimer | | | 6 | | | | 5 | | | |
| | Reaction product of (1) a docosahexaenoic acid dimer, (2) ethylbenzene sulfonic acid, and (3) a reaction product of a polyalkylene polyamine, a tall oil fatty acid, and a docosahexaenoic acid dimer | 7 | | | | | | | | | |
| Organic sulfur compound | 2-Mercaptoethanol | | | | | 4 | 1.2 | | 1.2 | | 1.9 |
| | Napthalenedisulfonic acid | | | 5 | | | | | | 1 | |
| | 3,6-dimethyl-1,2-benzenedisulfonic acid | | 4 | | | | | 1 | | | |
| | benzenedisulfonic acid | 5 | | | | 3 | | | | | |
| Demulsifier | Reaction product of ethylene oxide-propylene oxide copolymer and EPON ® epoxy resin | | | | | 3 | | 1 | | 1 | |
| | Polypropylene glycol | | | | | | 3 | 2 | | 2 | |
| | Dodecylbenzylsulfonic acid | | | | 4 | | | | | 0.5 | |
| Demulsifier | Sodium salt of xylenesulfonic acid | | 4 | | | | | | | | |
| | Phenolic resin | 5 | | | | | | | | | |
| | Acetic acid | | | | | | | | 2 | | 1.27 |
| Total | | 100 | 100 | 100 | 100 | 100 | 100 | 100 | 100 | 100 | 100 |

Some of the compositions were tested for corrosion inhibitor performance under the test conditions shown in Table 2. Carbon steel coupons were cleaned, degreased and weighed. They were then mounted in a PEEK holder and placed in an autoclave vessel after which a deaerated 5,000 ppm Cl— brine was added along with the gas compositions as shown in Table 2. The coupons were left to corrode for 24 hours without corrosion inhibitor in the presence of elemental sulfur and sodium tetrasulfide. After 24 hours, the brine was replaced with the brine shown in Table 2 along with the elemental sulfur, sodium tetrasulfide and corrosion inhibitor at the applicable dose and acid gas composition and left to corrode for a further 137 hours. The coupons were re-weighed and the corrosion rate determined by weight loss. The coupon surface was also microscopically profiled with a white light interferometer to determine the pitting attack.

TABLE 2

| | Conditions 1 | Conditions 2 |
|---|---|---|
| Metallurgy | C1018 | C1018 |
| Initial surface finish | Pre-corroded | Pre-corroded |
| Brine TDS (ppm) | 113,000 | 83,000 |

TABLE 2-continued

|  | Conditions 1 | Conditions 2 |
| --- | --- | --- |
| Temperature (° C.) | 50 | 50 |
| PH$_2$S (psi) | 112 | 37 |
| PCO$_2$ (psi) | 33 | 14.7 |
| % H$_2$S of acidic gases | 77 | 71.5 |
| Sodium tetrasulfide (ppm) | 1,000 | 1,000 |
| Elemental sulfur (ppm) | 770 | 770 |
| Test duration (h) | 137 | 137 |

The corrosion pass criteria were general corrosion of less than 0.1 mm/year, and a depth threshold for localized corrosion of no more than one random pit greater than 10 μm.

The corrosion test results for the first set of conditions are shown in Table 3. FIGS. 1-4 show the coupon surface after the corrosion test (panel A), a WLI microscopic image of the coupon surface after the corrosion test (panel B), and a pit histogram indicating the total number of pits in a particular depth range for the coupon.

TABLE 3

| Composition Tested | Dose (ppm) | General Corrosion Weight Loss Rate (mm y$^{-1}$) | General Corrosion Weight Loss Rate | Pitting (Figure Number) | Pitting Corrosion | Overall Corrosion |
| --- | --- | --- | --- | --- | --- | --- |
| K (Comparative) | 5,000 | 0.29 | Fail | 1 | Fail | Fail |
| K (Comparative) | 10,000 | 0.19 | Fail | 2 | Fail | Fail |
| F | 5,000 | <0.01 | Pass | 3 | Pass | Pass |
| H | 5,000 | <0.01 | Pass | 4 | Pass | Pass |

The incumbent Comparative Composition K exhibited significant general and pitting corrosion at both 5,000 ppm and 10,000 ppm under these test conditions. Compositions F and H resulted in negligible general or pitting corrosion at half the dose of Comparative Composition K under the same test conditions.

Figure 5:
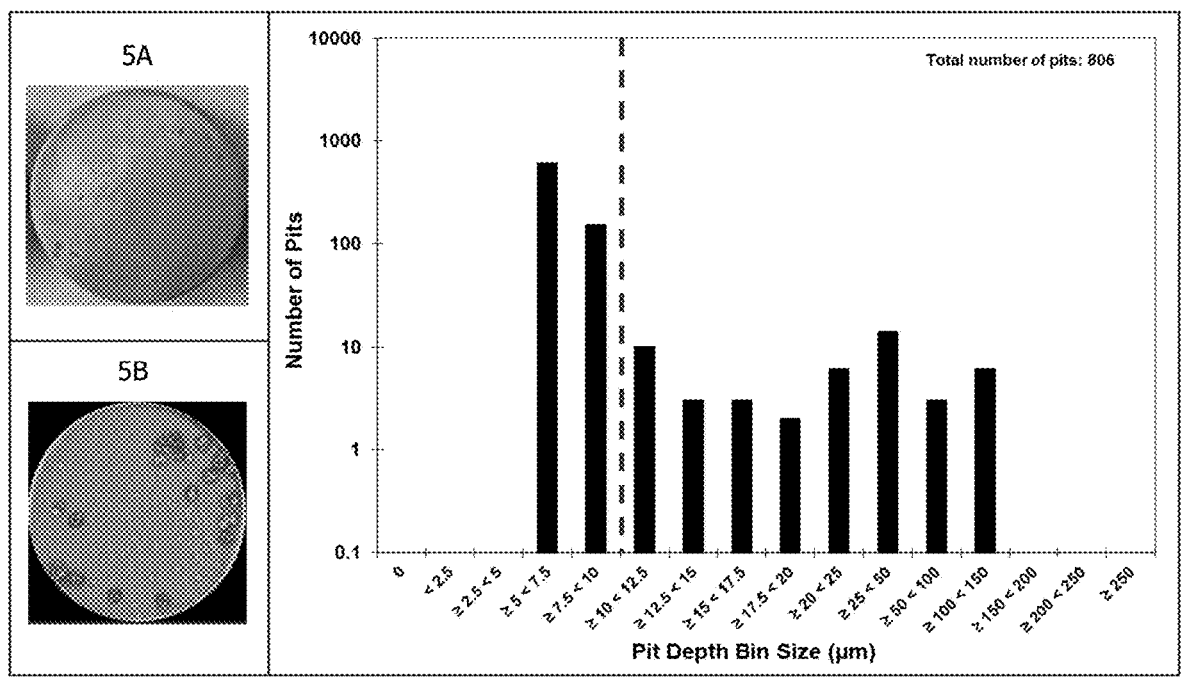
FIG. 5 shows a photograph of a coupon surface after corrosion testing (panel 5A), a WLI microscopic image of the coupon surface after corrosion testing (panel 5B), and a pit histogram indicating the total number of pits in a particular depth range for the coupon for Comparative Composition C under the second set of test conditions at 3,000 ppm concentration.
Figure 6:
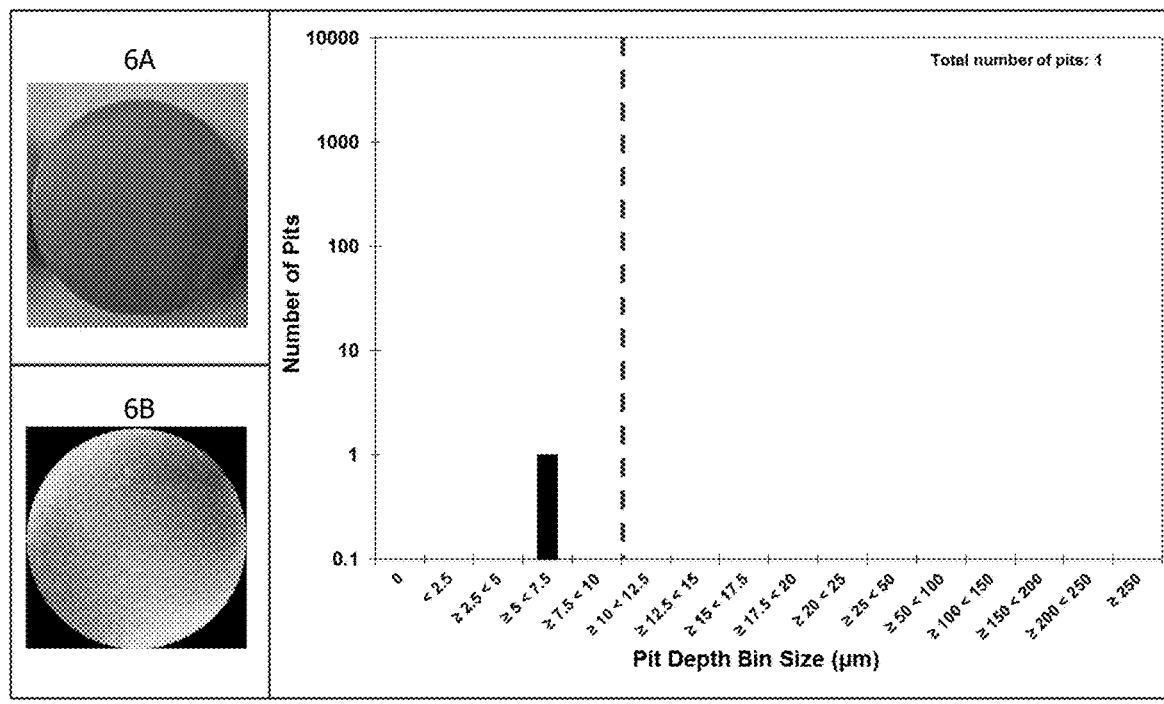
FIG. 6 shows a photograph of a coupon surface after corrosion testing (panel 6A), a WLI microscopic image of the coupon surface after corrosion testing (panel 6B), and a pit histogram indicating the total number of pits in a particular depth range for the coupon for Composition A under the second set of test conditions at 3,000 ppm concentration.

The corrosion test results for the second set of conditions are shown in Table 4. FIGS. 5 and 6 show the coupon surface after the corrosion test (panel A), a WLI microscopic image of the coupon surface after the corrosion test (panel B), and a pit histogram indicating the total number of pits in a particular depth range for the coupon.

TABLE 4

| Composition Tested | Dose (ppm) | General Corrosion Weight Loss Rate (mm y$^{-1}$) | General Corrosion Weight Loss Rate | Pitting (Figure Number) | Pitting Corrosion | Overall Corrosion |
| --- | --- | --- | --- | --- | --- | --- |
| J (Comparative) | 3,000 | 0.23 | Fail | 5 | Fail | Fail |
| F | 3,000 | 0.02 | Pass | 6 | Pass | Pass |

Composition F significantly outperformed Comparative Composition J. The aromatic hydrocarbon solvent and the salt of a fatty acid-amine condensate in Composition F effectively mitigated elemental sulfur and polysulfide corrosion attack in the sour system as compared to Comparative Composition J.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A corrosion inhibiting composition comprising a salt of a fatty acid-amine condensate and an aromatic solvent, wherein the salt of the fatty acid-amine condensate comprises a reaction product of (1) a polyunsaturated fatty acid dimer, (2) a sulfonic acid compound, and (3) a reaction product of a polyalkylene polyamine, a tall oil fatty acid, and a polyunsaturated fatty acid dimer.

2. The composition of claim 1 comprising:
   from about 2 to about 30 wt. % of the salt of the fatty acid-amine condensate;
   from about 1 to about 40 wt. % cationic surfactant;
   from about 1 to about 40 wt. % substituted aromatic amine;
   from about 1 to about 30 wt. % phosphoric acid ester;
   from 0 to about 20 wt. % solvent stabilizer compound;
   from 0 to about 5 wt. % demulsifier;
   from 0 to about 15 wt. % organic sulfur compound; and
   from about 40 to about 80 wt. % of the aromatic solvent.

3. The composition of claim 1, wherein the sulfonic acid compound comprises a linear alkyl benzene sulfonic acid.

4. The composition of claim 1, wherein the polyunsaturated fatty acid dimer comprises a linoleic acid dimer.

5. The composition of claim 1, wherein the composition further comprises a cationic surfactant, a solvent stabilizer, a phosphoric acid ester, an organic sulfur compound, a demulsifier, a substituted aromatic amine, or a combination thereof.

6. The composition of claim 5, wherein the composition further comprises the cationic surfactant, and the cationic surfactant comprises an alkoxylated alkyl amine, a quaternary ammonium compound, or a combination thereof.

7. The composition of claim 5, wherein the composition further comprises the solvent stabilizer, and the solvent stabilizer comprises a glycol ether.

8. The composition of claim 7, wherein the glycol ether comprises 2-butoxyethanol.

9. The composition of claim 5, wherein the composition further comprises the phosphoric acid ester, and the phosphoric acid ester comprises an alkoxylated alkylphenol phosphate ester.

10. The composition of claim 5, wherein the composition further comprises the organic sulfur compound, and the organic sulfur compound comprises a mercaptoalkyl alcohol.

11. The composition of claim 5, wherein the composition further comprises the demulsifier, and the demulsifier comprises an oxyalkylate polymer.

12. The composition of claim 11, wherein the oxyalkylate polymer comprises a polyalkylene glycol.

13. The composition of claim 1, wherein the solvent comprises xylene, heavy aromatic naphtha, toluene, or a combination thereof.

14. The composition of claim 5, wherein the composition further comprises the substituted aromatic amine, and either: the substituted aromatic amine comprises an alkyl pyridine; or the substituted aromatic amine comprises 3,5-diethyl-2-methylpyridine, 3-ethyl-4-methylpyridine, (E)-5-ethyl-2-(prop-1-en-1-yl)pyridine, (E)-5-(but-2-en-1-yl)-2-methylpyridine, N-ethyl-2-(6-methylpyridin-3-yl)ethanamine, or a combination thereof.

15. The composition of claim 2 comprising
from about 3 to about 20 wt. % of the salt of the fatty acid-amine condensate;
from about 1 to about 20 wt. % of the cationic surfactant;
from about 1 to about 20 wt. % of the substituted aromatic amine;
from about 1 to about 20 wt. % of the phosphoric acid ester;
from about 1 to about 15 wt. % of the solvent stabilizer compound;
from about 0.5 to about 5 wt. % of the demulsifier;
from 1 to about 10 wt. % of the organic sulfur compound; and
from about 50 to about 80 wt. % of the aromatic solvent.

16. The composition of claim 2 comprising
from about 4 to about 10 wt. % of the salt of the fatty acid-amine condensate;
from about 1 to about 10 wt. % of the cationic surfactant;
from about 1 to about 10 wt. % of the substituted aromatic amine;
from about 1 to about 10 wt. % of the phosphoric acid ester;
from about 1 to about 10 wt. % of the solvent stabilizer compound;
from about 0.5 to about 5 wt. % of the demulsifier;
from 1 to about 5 wt. % of the organic sulfur compound; and
from about 65 to about 80 wt. % of the aromatic solvent.

17. A method of reducing, inhibiting or preventing corrosion of a metal surface used in recovery, transportation, refining or storage of a hydrocarbon fluid containing elemental sulfur or polysulfide, the method comprising contacting the composition of claim 1 with the metal surface to reduce, inhibit or prevent corrosion of the metal surface.

18. The method of claim 17, wherein either: the composition is added to the hydrocarbon fluid before the hydrocarbon fluid contacts the metal surface; the hydrocarbon fluid contains at least 500 ppm elemental sulfur; the composition is added to the hydrocarbon fluid at a concentration of about 100 to about 1,000,000 ppm; or the metal surface comprises a carbon steel conduit or pipeline.

19. The method of claim 18, wherein the composition is added to the hydrocarbon fluid at a concentration of about 500 to about 100,000 ppm.

20. A method of reducing, inhibiting or preventing corrosion of a metal surface used in recovery, transportation, refining or storage of a hydrocarbon fluid containing elemental sulfur or polysulfide, the method comprising contacting the composition of claim 2 with the metal surface to reduce, inhibit or prevent corrosion of the metal surface.

* * * * *